(12) United States Patent  
Chowdhury

(10) Patent No.: US 9,770,578 B2
(45) Date of Patent: Sep. 26, 2017

(54) DEVICES FOR TRANSDERMAL DRUG DELIVERY

(75) Inventor: Dewan Fazlul Hoque Chowdhury, Loughborough (GB)

(73) Assignee: NDM Technologies Limited, Loughborough (GB)

(*) Notice: Subject to any disclaimer, the term of this patent is extended or adjusted under 35 U.S.C. 154(b) by 374 days.

(21) Appl. No.: 13/822,554

(22) PCT Filed: Sep. 13, 2011

(86) PCT No.: PCT/GB2011/051716
§ 371 (c)(1),
(2), (4) Date: Mar. 12, 2013

(87) PCT Pub. No.: WO2012/035334
PCT Pub. Date: Mar. 22, 2012

(65) Prior Publication Data
US 2013/0178830 A1    Jul. 11, 2013

(30) Foreign Application Priority Data
Sep. 13, 2010    (GB) .................................. 1015164.5

(51) Int. Cl.
*A61M 37/00*    (2006.01)
(52) U.S. Cl.
CPC . *A61M 37/0015* (2013.01); *A61M 2037/0023* (2013.01); *A61M 2037/0046* (2013.01)
(58) Field of Classification Search
CPC ...... A61M 37/0015; A61M 2037/0023; A61M 37/0076; A61M 37/0084;
(Continued)

(56) References Cited

U.S. PATENT DOCUMENTS 1,699,012 A * 1/1929 Naylor ................. A01K 11/005
                                                        101/26
6,589,202 B1 * 7/2003 Powell .......................... 604/27
(Continued)

FOREIGN PATENT DOCUMENTS

JP        S60129057        7/1985
WO      WO 0149346        7/2001
(Continued)

OTHER PUBLICATIONS

European Patent Office International Preliminary Report on Patentability and Written Opinion dated Mar. 19, 2013 for PCT/GB2011/051716 (7 pages).
(Continued)

*Primary Examiner* — Bhisma Mehta
*Assistant Examiner* — Hamza Darb
(74) *Attorney, Agent, or Firm* — McCracken & Gillen LLC

(57) ABSTRACT

A transdermal drug delivery device comprises needles (10) for piercing the skin (4) of a patient to form pores (20) in a predefined pattern; and carriers (12) in the same pattern that may be loaded with a drug (14) for delivery. The carriers (12) are applied to the pores (20) to deliver the drug (14) through the pores (20) to a location beneath the surface of the skin (4). The carriers (12) may remain outside the pores (20), be introduced into the pores (20) after the needles (10) have been removed or be inserted alongside the needles (20) while they are still in place.

10 Claims, 5 Drawing Sheets

Figure 1A:
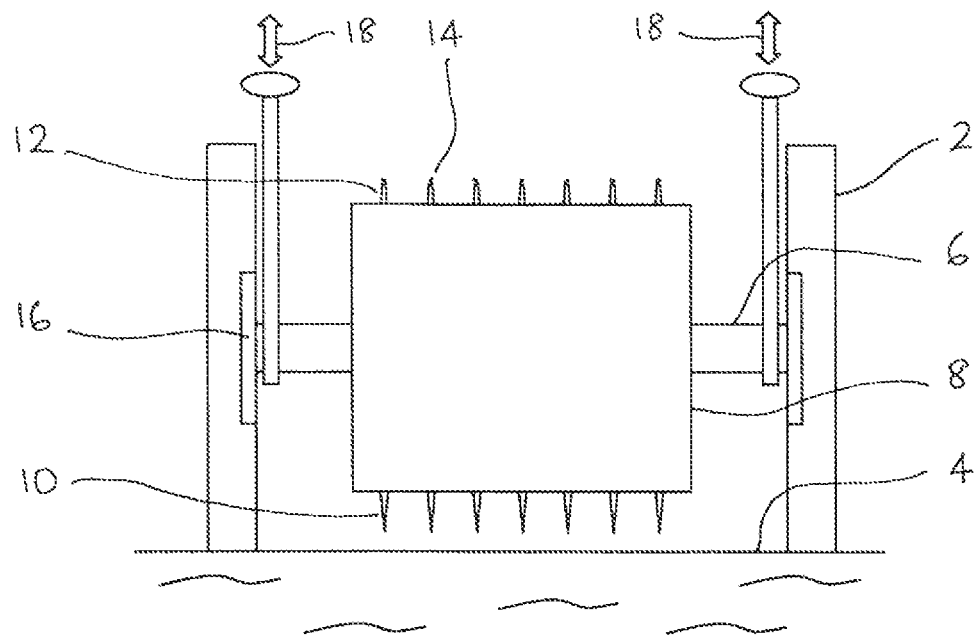

(58) Field of Classification Search
CPC .. A61M 2037/0061; A61M 2037/0046; A61B 5/411
USPC ............ 604/173, 511, 44-48, 93.01, 131; 600/556
See application file for complete search history.

(56) References Cited

U.S. PATENT DOCUMENTS

| | | | |
|---|---|---|---|
| 6,611,707 B1* | 8/2003 | Prausnitz | A61B 5/14514 604/21 |
| 2007/0106207 A1* | 5/2007 | Withey | A61B 17/205 604/46 |
| 2007/0129714 A1* | 6/2007 | Elkins et al. | 606/21 |
| 2008/0221407 A1* | 9/2008 | Baker | A61B 5/14514 600/309 |
| 2009/0099502 A1* | 4/2009 | Tokumoto et al. | 604/21 |
| 2009/0234301 A1 | 9/2009 | Tomono | |
| 2012/0123387 A1* | 5/2012 | Gonzalez et al. | 604/506 |

FOREIGN PATENT DOCUMENTS

| | | |
|---|---|---|
| WO | WO 0202180 | 1/2002 |
| WO | WO 2008004781 | 1/2008 |
| WO | WO 2008091878 | 7/2008 |
| WO | WO 2008125798 | 10/2008 |
| WO | WO 2009072811 | 6/2009 |

OTHER PUBLICATIONS

European Patent Office Search Report dated Jan. 4, 2012 for PCT/GB2011/051716 (3 pages).
Japanese Examination Report, with English language translation, issued on Nov. 30, 2016, for Japanese Application No. 2016-008439, filed Jan. 20, 2016, for Applicant, NDM Technologies Ltd. (6 pages).

* cited by examiner

DEVICES FOR TRANSDERMAL DRUG DELIVERY

TECHNICAL FIELD

The invention relates to the field of transdermal delivery of drugs into the body of a patient. In particular, it relates to the delivery of drugs through pores previously created in the skin.

For the sake of brevity, the term "drugs" is used in this specification to refer to any biologically active substances that may need to be introduced into the body of a patient to provide a therapeutic, cosmetic or nutritional effect. The patient may be human or a non-human animal, "Transdermal" refers to delivery through the skin of the patient or through any other accessible surface tissue such as the cornea or the inside of the mouth cavity.

BACKGROUND OF THE INVENTION

Methods have been described for enhancing skin permeation of drugs by using a device that gradually eases microneedles into contact with the skin, for example by forming an array of microneedles directly on a roller or, as described in international patent application WO 2008/125798, by forming an array of microneedles on a patch secured to a belt that travels over a set of rollers. This method has been demonstrated to be superior to simply pressing a flat array of microneedles against the skin. That is because less insertion force is required and because, given that the array of needles is inserted row by row, the reproducibility of the dose is also increased independently of the operator.

The main barrier to delivery of drugs through the skin is the stratum corneum, which is a tough outer layer of dead skin cells. The microneedles may be hollow to provide a channel for delivery of a fluid drug through the stratum corneum or they may be solid and simply coated with the drug for delivery. Alternatively, a device comprising solid microneedles may be used to disrupt the stratum corneum and/or to create pores through it in order to enhance its permeability to a drug that is subsequently applied to the surface of the skin, for example in the form of a gel or in a patch. However, because the needles only perforate a small proportion of the surface area of skin being treated, a majority of the subsequently applied drug formulation does not enter the pores but remains on the surface of the skin. This is contrary to the requirements of most bodies governing drug registration that minimal drug should be applied, and that minimal excess should be present after application. It is also wasteful of a potentially expensive product.

SUMMARY OF THE INVENTION

The invention provides a transdermal drug delivery device as defined in claim 1. The invention further provides a method of transdermal drug delivery as defined in claim 18. Preferred but non-essential features of the invention are defined in the dependent claims.

By delivering the drug only to the locations of the previously formed pores, a controlled quantity of the drug formulation can be delivered to precisely where it can travel through the pores to penetrate the stratum corneum and be taken up by the body. There will be minimal wastage of drug left on the surface of the skin and inaccessible to the body. The drug may be delivered to the mouths of the pores, especially if it is in a fluid state. Preferably the drug is positioned by the carriers directly inside the pores, beneath the stratum corneum, from where it can be diffused and dispersed through the body like other transdermally delivered treatments. This is suitable for drug formulations in various states, including solid (powdered or particulate) drugs.

The simplest means for forming pores in the skin comprises a plurality of needles. A common mechanism can then be used to position the needles and the drug carriers to ensure a consistent alignment between them. However, other mechanical or non-mechanical means may be used for forming pores in predetermined locations on the skin, for example laser ablation.

THE DRAWINGS

Figure 1B:
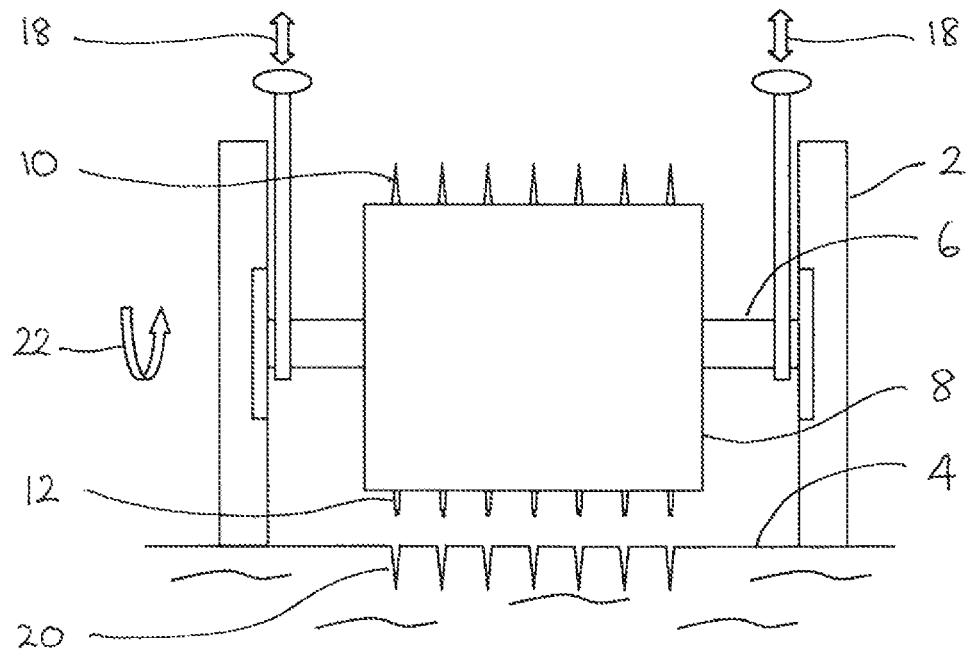

FIGS. 1*a* and 1*b* illustrate two steps in the process of delivering drugs to a patient using a device according to a first embodiment of the invention.

Figure 2A:
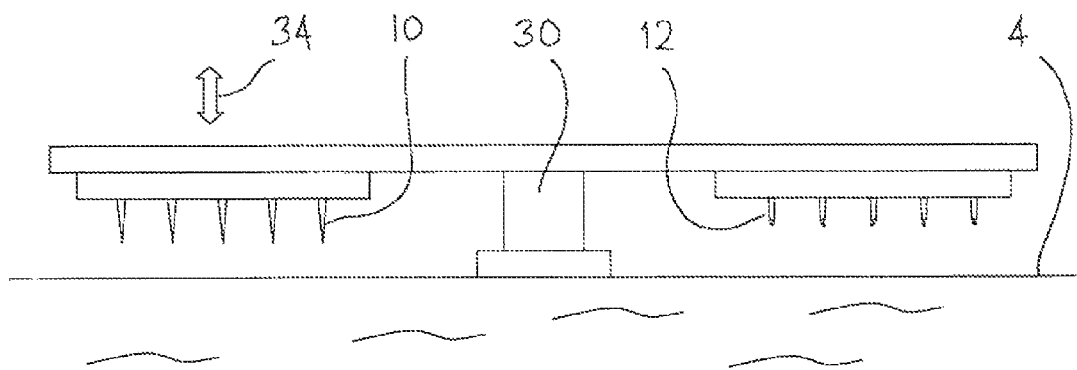

FIGS. 2*a* and 2*h* illustrate two steps in the process of delivering drugs to a patient using a device according to a second embodiment of the invention.

FIGS. 3*a* to 3*d* illustrate four steps in the process of delivering drugs to a patient using a device according to a third embodiment of the invention.

Figure 4A:
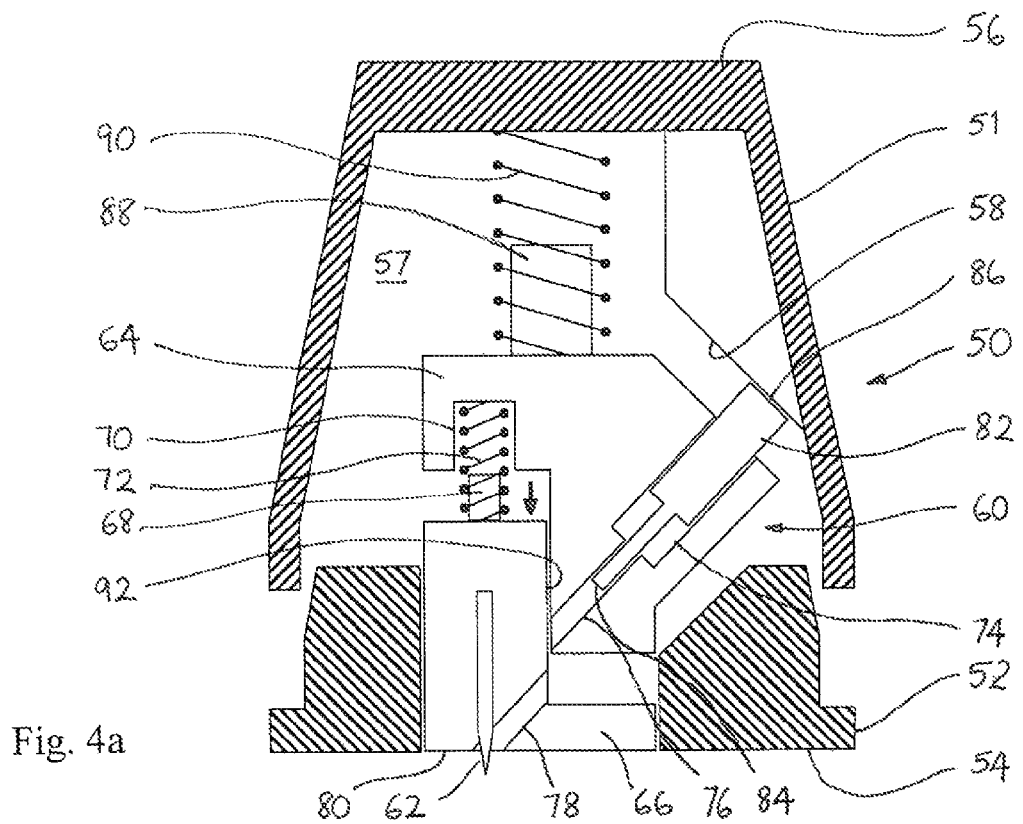
Figure 4B:
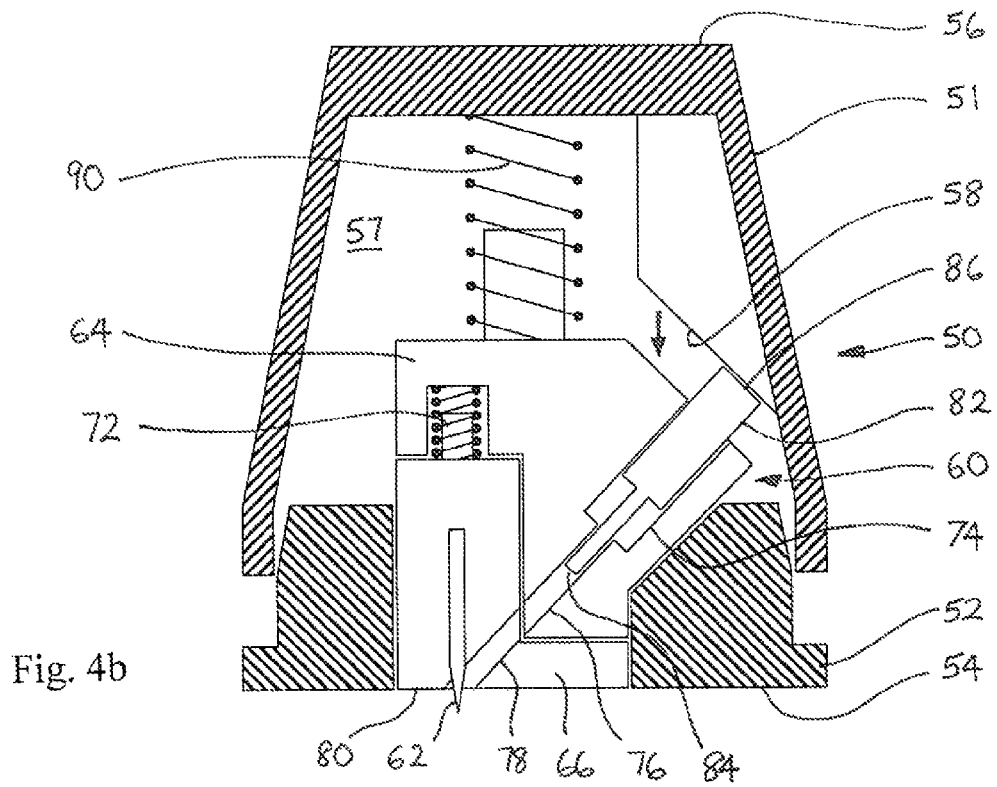
Figure 4C:
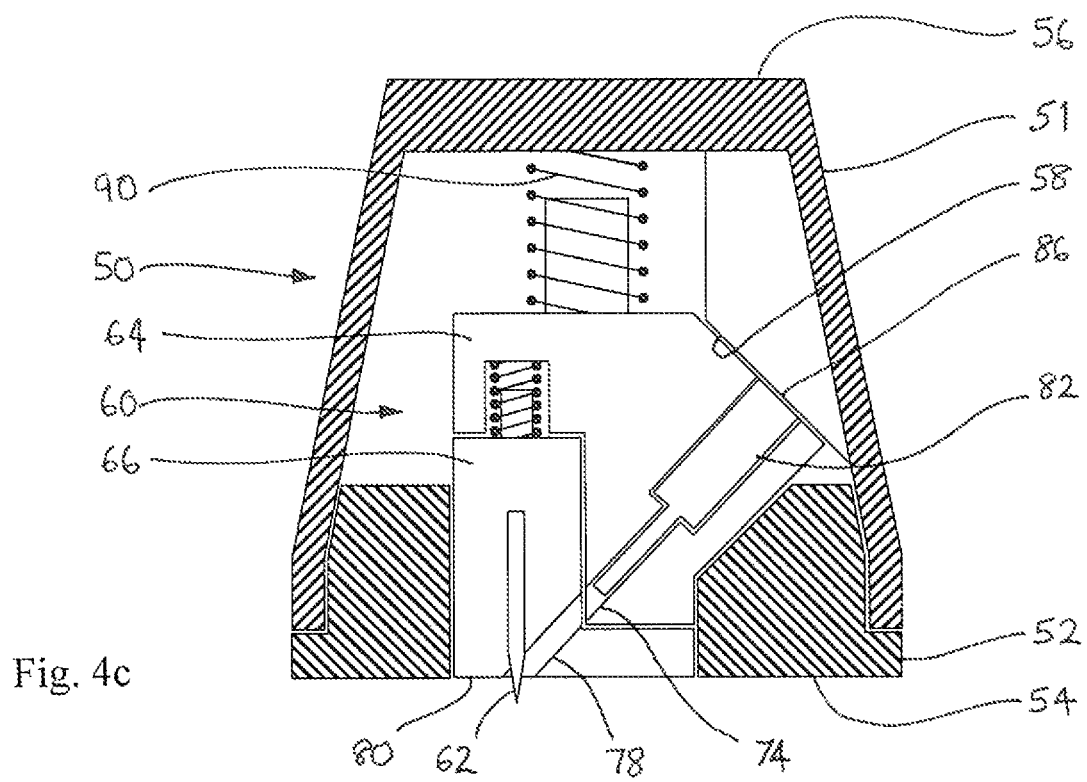

FIGS. 4*a* to 4*c* illustrate three steps in the process of delivering drugs to a patient using a device according to a fourth embodiment of the invention.

FIGS. 1*a* and 1*b* are schematic views of a transdermal drug delivery device comprising a frame 2 that is held in a fixed position on a treatment area of the skin 4 of a patient. An exchange means such as an axle 6, having an axis, extends between opposite sides of the frame 2 in an orientation generally parallel to the surface of the skin 4. The axle carries a block 8 with an array of microneedles 10 on one face and an array of microstructures 12 on the opposite face. The two arrays 10, 12 share an identical layout. In the side view of FIG. 1, only a single row of microneedles 10 and a single row of microstructures 12 are visible but in practice each array will extend over a two-dimensional surface of the block 8.

The microneedles 10 may be formed using any suitable method such as moulding or micro-machining. They may have a diameter in the range from a few tens of micrometres to more than a millimetre; and a length typically a few times greater than their width. The length is preferably sufficient to penetrate the stratum corneum of the skin but not great enough for the needles to reach the nerve endings that are deeper in the skin.

The microstructures 12 are preferably elongate elements such as rods or posts. Unlike conventional microneedles, these are formed to have blunt tips. The tips are preferably flat, i.e. generally planar and perpendicular to the long axes of the microstructures 12. The microstructures 12, like the microneedles 10, may be produced from any suitable type of plastic, ceramic or metal, and should be of a dimension and shape that allows the insertion of the drug directly into the pore created by the microneedle. To achieve this the microstructure may either remain above the stratum corneum, acting purely to force the drug through the pore, or it may be shaped such that it is able to penetrate the pore already created by the microneedle thus delivering the drug directly to a deeper region within the skin. The microstructure may thus be smaller than the pore created by the microneedle to allow it to be inserted into the skin as it forces the drug through, or it may be angled or bevelled such that although the microstructure may be larger than the pore created, or larger than the needles used to create the pores, it will still be able to penetrate the pore and push the drug deeper into the skin, A drug in any suitable formulation may be loaded onto the tips of the microstructures 12. If the formulation is in solid form, one or more particles 14 of it may be attached to the tips by using an adhesive in which the particles are insoluble. The particles 14 may alternatively be attached through electrostatic attraction to avoid the use of any adhesive that may cause degradation or weakening of the particles during storage. Static charge will be concentrated at the tips of the carriers and may encourage the particles 14 to attach there. Metallic based particles may be loaded on to the tips of the microstructures using magnetic attraction.

Each end of the axle 6 of the drug delivery device is mounted in a means for moving each carrier such as a mechanism 16 that permits the axle 6 to move towards and away from the skin 4 of the patient. The movement towards the skin may be effected by manual pressure, as shown by the pair of double-headed arrows 18 in FIGS. 1a and 1b. The movement may be guided by a slot (not shown); and return springs (not shown) may be provided to retract the axle 6 away from the skin 4 to its rest position. It will be understood that the drawing is purely schematic. In practice, a cover would have to be provided to prevent accidental contact by the user with the upwardly facing microneedles 10 or microstructures 12. A mechanism could be provided to ensure that the axle 6 remains level. The movement of the axle 6 towards and away from the skin could be automated instead of being effected manually; and means could be provided to regulate the force of impact with the skin 4.

This "stamping" action is first carried out with the microneedles 10 facing the skin 4, as shown in FIG. 1a to pierce the stratum corneum and create an array of pores 20, shown in FIG. 1b. The block 8 is then rotated through 180° about the axle 6, as shown by a curved arrow 22, so that the microstructures 12 are now facing the skin 4 and perfectly aligned with the pre-formed pores 20. The same stamping action is then repeated so that the microstructures 12 enter the respective pores 20 and each deposits its load of drug 14 at a predetermined depth within the pore 20.

The block 8 is not limited to a single array of microneedles 10 and a single array of microstructures 180° apart. There could be multiple such arrays angularly distributed about the surface of a cylinder or the faces of a prism. Indexing means would then be provided for turning the block 8 manually or automatically through an appropriate angle to ensure the precise orientation of the block 8 with the desired type of array facing the skin 4. In this manner more than one type of drug could be successively delivered into a single set of pores 20.

The arrays of microneedles 10 and microstructures 12 could be formed as separate patches for attachment to the surface of the block 8, provided they can be positioned sufficiently accurately. Alternatively, the arrays could be provided alternately along the surface of a belt (not shown) that is wrapped around a cylindrical block 8, with means for rotating the cylinder to advance the belt through a predetermined distance and bring the next array to the correct position.

Figure 2B:
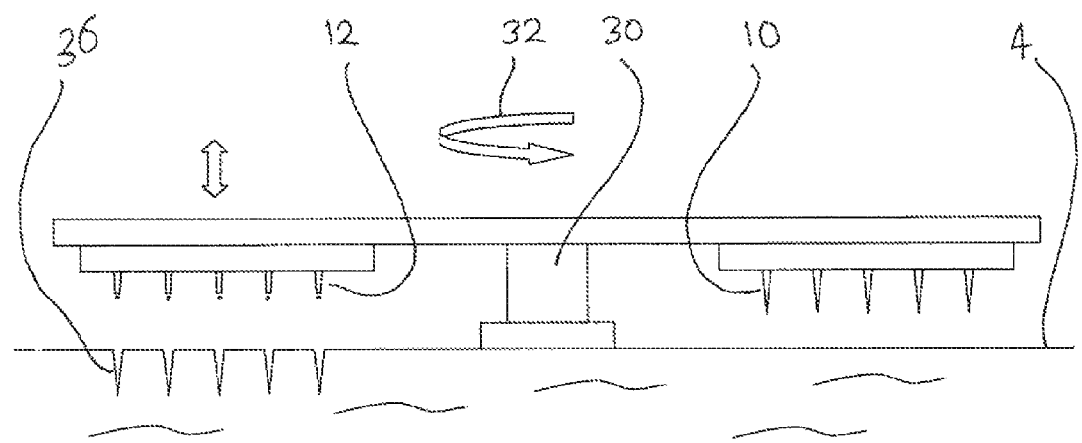

FIGS. 2a and 2b are schematic views of an alternative transdermal drug delivery device, in which the means for exchanging the arrays of microneedles 10 and microstructures 12 involves rotation about an axle 30, having an axis that is generally perpendicular to the skin 4, as shown by the curved arrow 32. Means (not shown in detail) are provided to permit the left hand array (as viewed in the drawings) to come into contact with the skin 4 and then be withdrawn, in a similar stamping action to that previously described, as indicated by the double-headed arrows 34. First the array of microneedles 10 are pushed into the skin 4 and retracted to form pores 36. Then the device is rotated about its axle 30 to bring the array of microstructures 12 carrying the drug particles 14 into coincidence with the pores 36 and the stamping action is repeated to deliver the drug into the pores 36.

The axle 30 may be constructed so as to be capable of compression telescopically to bring the left hand array into contact with the skin, with a return spring (not shown) to return the array to its rest position. If the skin is flat, such an arrangement would tend to bring the right hand array simultaneously into contact with a different area of the skin, which must be avoided. Means could be provided to shield the skin in that area or the device could be configured so that the right hand array is higher than the left hand array, for example by angling the axle 30 slightly away from the vertical while keeping the active array on the left parallel to the surface of the skin.

Not only rotational motion is capable of exchanging the positions of the arrays. A device in accordance with the invention could allow the array of microneedles 10 to slide out of position and the array of microstructures 12 to slide into position, preferably both in a single movement.

FIGS. 3a to 3d show a different embodiment of drug delivery device according to the invention, in which the microstructures 40 introduce the drug 42 into the pores 44 while the microneedles 46 that formed the pores 44 are still in place. The Figures show a single needle, which will typically but not exclusively form part of an array of identical needles.

Figure 3A:
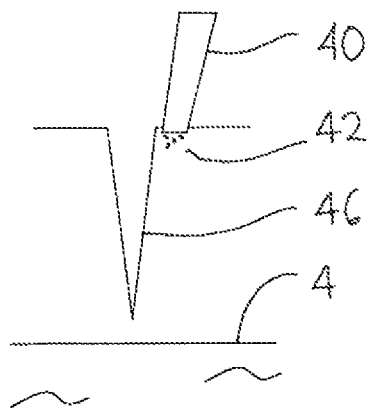
Figure 3B:
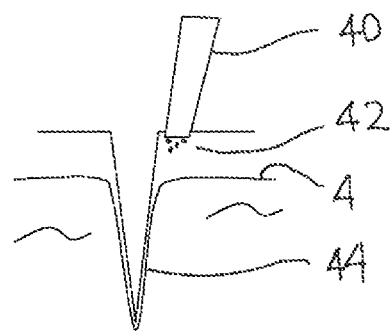

FIG. 3a shows a microneedle 46 poised above the skin 4 of a patient. A microstructure 40 has particles of a drug formulation 42 loaded onto its flat tip 48. (It is not necessary that the drug be in particulate or even solid form.) The microstructure 40 is in a retracted position so that the microneedle 46 can penetrate the surface of the skin 4 without the drug 42 coming into contact with the skin, as shown in FIG. 3b. The microneedle 46 forms a pore 44 through the outer layer of the skin 4.

Figure 3C:
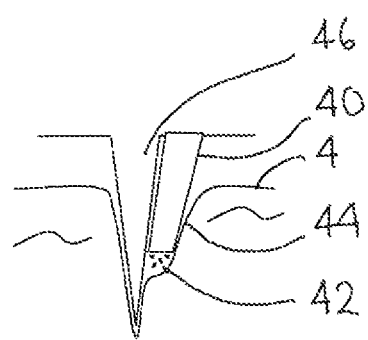
Figure 3D:
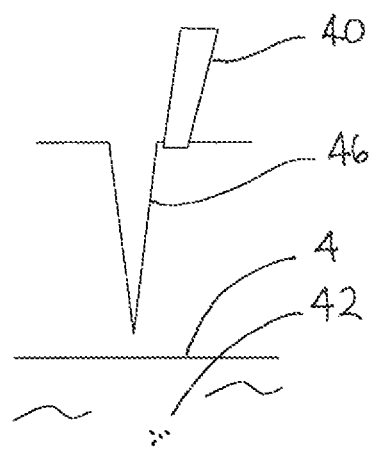

Next the microstructure 40 advances from the retracted position shown in FIG. 3b to the deployed position shown in FIG. 3c, travelling along the surface of the needle 46 and entering the pore 44 that has been firmed by the needle. The drug 42 can thereby be deposited into the pore 44 from the blunt tip 48 of the microstructure at a suitable depth to be absorbed by the patient. As shown in FIG. 3d, the microneedle 46 and the microstructure 40 can then both be withdrawn from the skin, which quickly closes up the pore, leaving the embedded drug 42.

In the embodiment of FIGS. 3a to 3d, the microneedles need not be cylindrical/conical but can have a flattened cross-section or be generally wedge-shaped to present one or more flat side faces. This provides a larger surface against which the microstructure 40 can bear. The side face of the microneedles may also be provided with at least one longitudinal groove, which provides space within the pore 44 for the drug to be accommodated and encourages the drug to flow down the groove deeper into the skin.

FIGS. 4a to 4c show schematically a cross-section through a hand-held device according to a further embodiment of the invention. The device comprises an outer case 50 that is formed from two parts, namely an upper part 51 and a lower part 52. The upper and lower parts 51,52 engage one another so as to be capable of relative sliding movement in the vertical direction (as illustrated). That movement is regulated by compression springs, as will be discussed below. A generally flat lower face 54 of the lower part 52 is intended to rest against the skin of a patient during use of the device. An upper face 56 of the upper part 51 is intended to be pressed by the hand of a user and may be generally flat or curved so as to provide additional comfort or control. The upper and lower parts 51,52 of the case form a cavity 57 between them. A cam surface 58 projects from an interior wall of the upper part 51 into the cavity 57.

A central opening in the lower face 54 of the case is shaped so that it can receive a disposable insert 60. Means such as a catch or clip (not shown) hold the insert in position in the device during use and can then be manually released to allow the insert 60 to be removed and replaced. When in position in the device, the insert 60 lies entirely within the boundary, of the case, except that a row of needles 62 is mounted in the insert and the tips of the needles project just below the lower face 54 so that they can penetrate the outer layer of a patient's skin. (The row of needles 62 extends perpendicularly to the plane of FIGS. 4*a*-4*c* so only one of them is visible. If the drug to be delivered is sufficiently potent, it may be that only a single needle is required, instead of a row of them.)

The insert 60 is formed from two parts, namely an upper part 64 and a lower part 66. The upper and lower parts 64,66 engage one another so as to be capable of relative sliding movement in the vertical direction (as illustrated). A peg 68 on an upper surface of the lower part 66 of the insert is aligned with a recess 70 in a lower surface of the upper part 64 of the insert. The peg 68 and the recess 70 provide seating for a first compression spring 72. (It will be understood that the positions of the peg 68 and the recess 70 could be exchanged or that other means of seating the spring 72 could be employed)

A set of angled channels 74 is formed in the insert 60. There is one channel 74 corresponding to each of the needles 62. Each channel 74 comprises an upper channel 76 formed in the upper part 64 of the insert and a lower channel 78 formed in the lower part 66 of the insert. Each lower channel 78 intersects the lower face 80 of the insert 60 at approximately the point where the corresponding needle 62 emerges. Located in each upper channel 76 is an elongated drug carrier 82. A tip 84 of the carrier occupies substantially the whole cross-section of the channel 76. An upper end 86 of the carrier projects from the insert 60 into the cavity 57 of the upper case 51. As shown, the upper end 86 may be wider than the tip to provide a surface to which a force can readily be applied. Under the influence of that force, the carrier 82 can slide along the upper channel 76.

A peg 88 on an upper surface of the upper part 64 of the insert provides seating for a second compression spring 90, which acts between the insert 60 and an interior wall of the upper part 51 of the outer case 50. The second spring 90 may be seated in a recess (not shown) in the case and it will be understood that the positions of the peg 88 and the optional recess could be exchanged or that other means of seating the spring 90 could be employed.

FIG. 4*a* shows the device in its rest configuration, when the first and second compression springs 72,90 are maximally extended. The upper part 51 of the outer case 50 is spaced from the lower part 52. The upper part 64 of the insert 60 is spaced from the lower part 66 and as a result the upper portion 76 of each channel 74 is not aligned with the lower portion 78. The carrier 82 is partially withdrawn from the upper channel 76 so that its upper end 86 projects into the cavity 57 and is close to or in engagement with the cam surface 58. A dose of drug (not shown) is loaded in each of the upper channels 76 and is contained by the tip 84 of the drug carrier 82 at its upper end and by an opposing wall 92 of the lower part 66 of the insert so that the drug cannot escape from the insert 60 during transport and storage.

To use the device and deliver the drug to a patient, manual pressure is applied to the top face 56 of the outer case 50. This causes the needles 62 to penetrate the outer surface of the patient's skin and form pores through which the drug may enter. The first compression spring 72 is weaker than the second compression spring 90 so that as the manual pressure continues it is the first compression spring 72 that is compressed first, as shown in FIG. 4*b*. This brings the upper and lower parts 64,66 of the insert 60 into contact and causes the upper and lower portions 76,78 of the angled channels 74 to align with one another, releasing the drug that has been contained in the upper channel 76 to flow into the lower channel 78.

As additional pressure is applied to the top face 56 of the outer case 50, the engagement between the upper and lower parts 64,66 of the insert 60 prevents further compression of the first compression spring 72 so the second compression spring 90 then begins to be compressed. This allows the upper part 51 of the outer case 50 to move towards the lower part 52. In so doing, the cam surface 58 begins to act against the upper ends 86 of the drug carriers 82 and forces each carrier 82 to slide along its upper channel 74 and to expel the drug therefrom towards the lower channel 78 in the manner of a piston. The lower end of the lower channel 78 is now aligned with the pore that has been formed by the needle 62 so that the drug is delivered directly to the pore, where it can be taken through the patient's skin.

FIG. 4*c* shows the configuration when the second spring 90 has been maximally compressed, the drug carrier 82 has been pushed fully into the channel 74 and the upper part 51 of the outer case 50 has come into engagement with the lower part. A catch (not shown) may be provided to maintain the device in this fully compressed configuration after use so that it is obvious that it has been used and no attempt will be made to re-use it until the insert 60 has been replaced with a new dose of drug.

It will be noted that in this embodiment of the invention the drug does not have to be adhered to the tip 84 of the carrier because the location of the drug is controlled by the channel 74. Thus the drug can optionally be in fluid form. Also, the tip 84 of the carrier does not necessarily have to approach the associated pore in the skin very closely, provided that it pushes the drug sufficiently far ahead of it to reach the pore.

Although the needles 62 are shown as fixed to the insert 60 and permanently extending from its bottom face 80, means (not shown) may be provided for shielding the tips of needles 62 or for keeping them retracted inside the insert 60 until the device is ready for use. The retracted needles may then be either extended manually or extended automatically when pressure is applied to the top face 56 of the outer case 50. For example, the needles could be mounted on the upper part 64 of the insert 60 and run through guides in the lower part 66. Then, as the two parts 64,66 move together in changing from the configuration of FIG. 4*a* to that of FIG. 4*b*, the needles will move along the guides until their tips project from the bottom face 80.

The invention claimed is:

1. A transdermal drug delivery device comprising:
   a number of needles for piercing skin of a patient to form a number of pores in the skin without delivering a drug to the skin;

a number of carriers for loading with a drug to be delivered; and means operable following removal of the number of the needles from the skin for moving each carrier to a corresponding pore of the previously formed pores to apply the carrier to the corresponding pore and deliver the drug to the corresponding pore.

2. The transdermal drug delivery device according to claim 1, wherein the number of carriers is equal to the number of pores.

3. The transdermal drug delivery device according to claim 1, wherein the number of needles is equal to the number of pores.

4. The transdermal drug delivery device according to claim 1, wherein a plurality of the number of needles is configured in a first array and wherein a plurality of the number of carriers is configured in a second array having the same layout as the first array.

5. The transdermal drug delivery device according to claim 4, further comprising exchange means for moving the first array away from a treatment position and for moving the second array into the treatment position.

6. The transdermal drug delivery device according to claim 5, wherein the exchange means comprises an axis about which the first and second arrays are rotated, the axis being generally parallel to the surface of the skin.

7. The transdermal drug delivery device according to claim 1, wherein each carrier is an elongate element having a tip that is capable of being loaded with the drug for delivery.

8. The transdermal drug delivery device according to claim 7, wherein the tip of each carrier is blunt.

9. A method of transdermal drug delivery comprising the steps of:

loading a number of carriers with a drug to be delivered;

piercing skin of a patient with a number of needles to form a number of pores in the skin without delivering the drug to the skin;

removing the number of needles from the skin; and following removal of the number of needles from the skin, moving each carrier to a corresponding pore of the previously formed pores to apply the carrier to the corresponding pore and deliver the drug to the corresponding pore.

10. The method according to claim 9, wherein the step of moving each carrier to the corresponding pore comprises simultaneously applying a plurality of the number of carriers to a plurality of the number of pores.

* * * * *